United States Patent
Moshos et al.

(10) Patent No.: US 10,308,666 B2
(45) Date of Patent: Jun. 4, 2019

(54) 7-AMINOCEPHEM DERIVATIVE COMPOUNDS

(71) Applicant: Merck Sharp & Dohme Corp., Rahway, NJ (US)

(72) Inventors: Kristos Adrian Moshos, Belmont, MA (US); Valdas Jurkauskas, Cambridge, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/920,609

(22) Filed: Mar. 14, 2018

(65) Prior Publication Data

US 2018/0258101 A1   Sep. 13, 2018

Related U.S. Application Data

(62) Division of application No. 14/974,223, filed on Dec. 18, 2015, now abandoned.

(60) Provisional application No. 62/095,942, filed on Dec. 23, 2014.

(51) Int. Cl.
   *C07D 501/04*    (2006.01)
(52) U.S. Cl.
   CPC .................. *C07D 501/04* (2013.01)
(58) Field of Classification Search
   CPC .................................................. C07D 501/04
   See application file for complete search history.

(56) References Cited

U.S. PATENT DOCUMENTS

| 8,329,684 B2 | 12/2012 | Cho et al. |
| 8,809,314 B1 * | 8/2014 | He ................... C07D 501/60 514/203 |
| 2016/0176897 A1 | 6/2016 | Moshos et al. |
| 2017/0129906 A1 | 5/2017 | Moshos et al. |

FOREIGN PATENT DOCUMENTS

| EP | 1556389 | 3/2005 | |
| GB | 1467610 A * | 3/1977 | ........... C07D 501/18 |
| WO | 2005027909 A1 | 3/2005 | |
| WO | 2014152763 A1 | 9/2014 | |
| WO | WO2016025813 | 2/2016 | |
| WO | WO2016025839 | 2/2016 | |
| WO | WO2016095860 | 6/2016 | |
| WO | WO2016100897 | 6/2016 | |
| WO | WO2016109259 | 7/2016 | |

OTHER PUBLICATIONS

U.S. Appl. No. 14/674,223, filed Dec. 18, 2015.

* cited by examiner

*Primary Examiner* — Sarah Pihonak
(74) *Attorney, Agent, or Firm* — J. Eric Thies; John C. Todaro

(57) ABSTRACT

This disclosure provides methods of making certain 7-aminocephem derivatives useful in the manufacture of cephalosporin antibiotic compounds.

14 Claims, 13 Drawing Sheets

*Biorg. Med. Chem. Lett.* 18 (2008) 4849-4852

XII → XIII 1.1  R:C$_5$H$_5$N, R:PCl$_5$, S:CH$_2$Cl$_2$, 30 min, 5°C
1.2  4 h, 5°C; 5°C → -25°C
1.3  S:MeOH, 2 h, rt

7-AMINOCEPHEM DERIVATIVE COMPOUNDS

This application is a Division of application Ser. No. 14/974,223, filed Dec. 18, 2015, which claims the benefit under 35 U.S.C. § 119(e) of U.S. Provisional Application No. 62/095,942, filed Dec. 23, 2014, the contents of which is incorporated herein in its entirety by reference thereto.

TECHNICAL FIELD

This disclosure relates to the synthesis of chemical compounds, including intermediates such as 7-aminocephem derivatives useful in the manufacture of cephalosporins such as ceftolozane.

BACKGROUND

Ceftolozane is a cephalosporin antibacterial agent of the beta-lactam class (f-lactams), also referred to as CXA-101, FR264205, or by chemical names such as (6R,7R)-5-thia-1-azabicyclo[4.2.0]oct-2-ene-carboxylic acid, 3-[[4-[[[(2-aminoethyl)amino]carbamoyl]amino]-2,3-dihydro-3-imino-2-methyl-1H-pyrazol-1-yl]methyl]-7-[[(2Z)-2-(5-amino-1,2,4-thiadiazol-3-yl)-2-[(1-carboxy-1-methylethoxy)imino]acetyl]amino]-8-oxo; or (6R,7R)-3-[(5-amino-4-{[(2-aminoethyl)carbamoyl]amino}-1-methyl-H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of formula (VI) that can be formulated for intravenous administration or infusion.

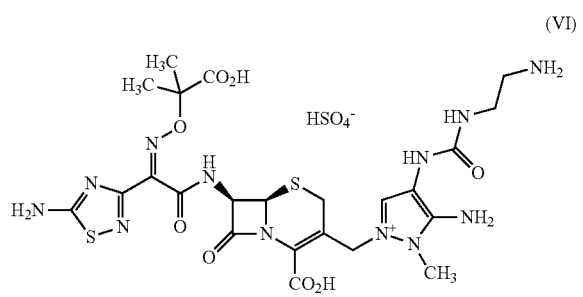 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; "HSO4-"]

(VI)

Ceftolozane sulfate is also referred to as: 1H-Pyrazolium, 5-amino-4-[[[(2-aminoethyl)amino]carbonyl]amino]-2-[[[(6R,7R)-7-[[(2Z)-2-(5-amino-1,2,4-thiadiazol-3-yl)-2-[(1-carboxy-1-methylethoxy)imino]acetyl]amino]-2-carboxy-8-oxo-5-thia-1-azabicyclo[4.2.0]oct-2-en-3-yl]methyl]-1-methyl-,sulfate (1:1); or 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate. Ceftolozane can be obtained as disclosed in U.S. Pat. No. 7,192,943 and in Toda et al., "Synthesis and SAR of novel parenteral anti-pseudomonal cephalosporins: Discovery of FR264205," *Bioorganic & Medicinal Chemistry Letters*, 18, 4849-4852 (2008), incorporated herein by reference. The antibacterial activity of ceftolozane is believed to result from its interaction with penicillin binding proteins (PBPs) to inhibit the biosynthesis of the bacterial cell wall which acts to stop bacterial replication.

Referring to FIG. 1, synthesis of ceftolozane can be performed via activation of the thiadiazolyl-oximinoacetic acid derivative (I) with methanesulfonyl chloride and $K_2CO_3$ in DMA at 10° C., followed by coupling with the 7-aminocephem (II) by means of $Et_3N$ in cold $EtOAc/H_2O$, affords amide (III). Substitution of the allylic chloride of compound (III) with 4-[(N-Boc-aminoethyl)carbamoylamino]-1-methyl-5-tritylaminopyrazole (IV) in the presence of 1,3-bis(trimethylsilyl)urea (BSU) and KI in DMF then affords the protected pyrazolium adduct (V), which, after full deprotection with trifluoroacetic acid in anisole/$CH_2Cl_2$, can be isolated as the hydrogensulfate salt by treatment with $H_2SO_4$ in i-$PrOH/H_2O$. The pyrazolyl urea intermediate (IV) can be prepared as follows referring to FIG. 2. Treatment of 5-amino-1-methylpyrazole (VII) with $NaNO_2/HCl$ in water at 5° C. gives the 4-nitrosopyrazole derivative (VIII), which can be reduced to the diaminopyrazole (IX) by catalytic hydrogenation over Pd/C in the presence of $H_2SO_4$. Selective acylation of the 4-amino group of compound (IX) with phenyl chloroformate in the presence of NaOH in $H_2O$/dioxane at 10° C. then yields the phenyl carbamate (X). After protection of the free amine group of carbamate (X) with chlorotriphenylmethane in the presence of $Et_3N$ in THF, the resulting N-trityl derivative (XI) can be coupled with N-Boc-ethylenediamine in the presence of $Et_3N$ in DMF to afford pyrazolyl urea (IV).

The 7-aminocephem compound (II) can be prepared according to the method disclosed in Chinese Patent No. 1634930, depicted in FIG. 3. However, this method results in the formation of impurities that are difficult to separate from the final product. Accordingly, there is a need for methods of preparing compound (II) that avoid the formation of impurities that are difficult to separate from the final product.

SUMMARY

Compound (II) (ACLE-HCl) may be prepared according to the method depicted in FIG. 3. It has now been discovered that 7-aminocephem compound (II) can be prepared from compound (IIa) according to the method depicted in FIG. 4. This method can proceed in higher yield than certain prior art methods and can avoid the formation of impurities such as methyl chloride and ethyl chloride. The preferred methods as disclosed in FIG. 4 are based in part on the discovery that the use of isobutyl alcohol avoids the formation of impurities such as methyl chloride and ethyl chloride. The method of the invention is also based in part on the discovery that careful control of the reaction temperature at particular stages can prevent epimerization and reformation of starting material.

DETAILED DESCRIPTION

Figure 1:
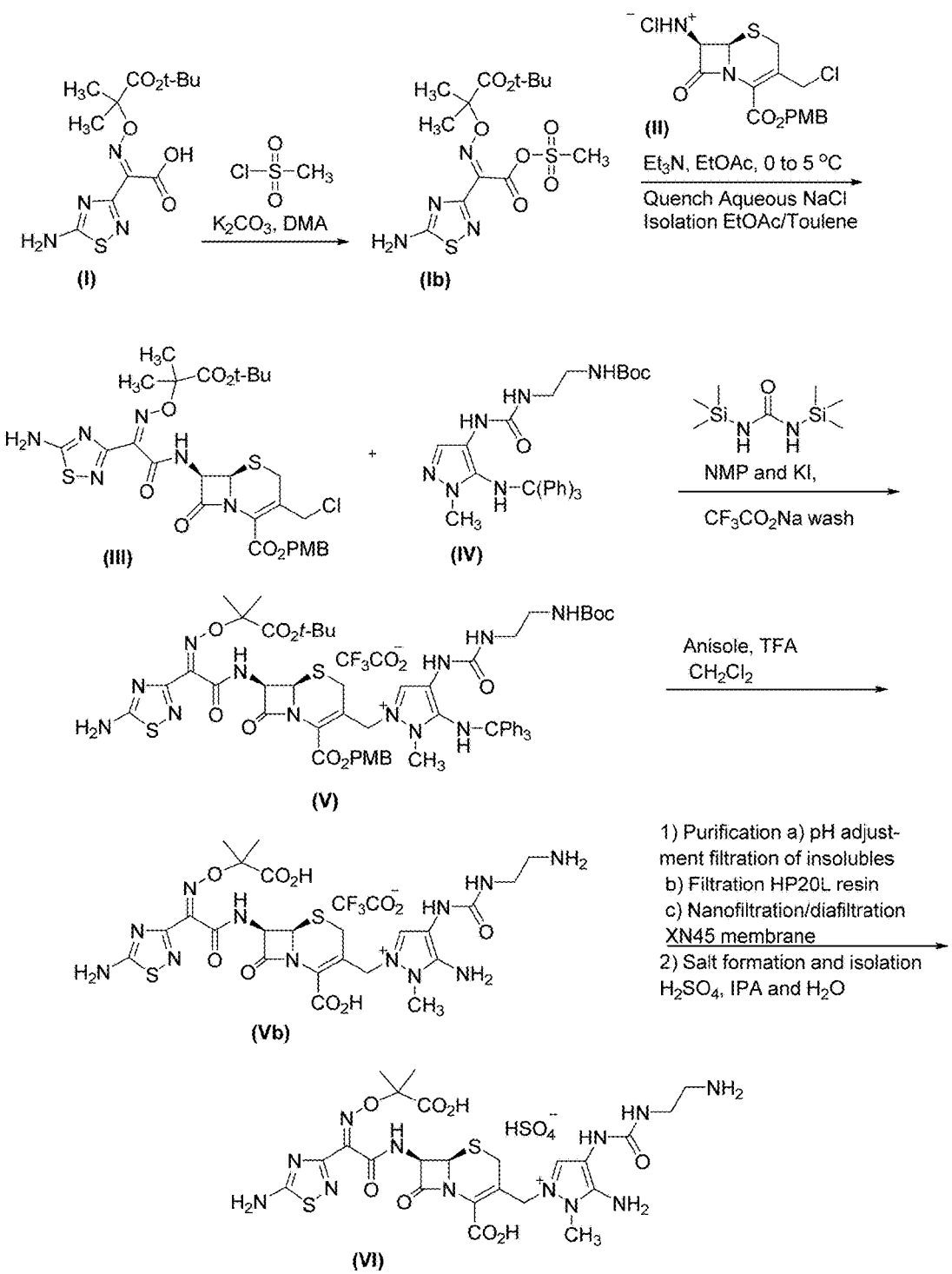
FIG. 1 shows a synthetic scheme to prepare compound (VI) (ceftolozane sulfate).
Figure 2:
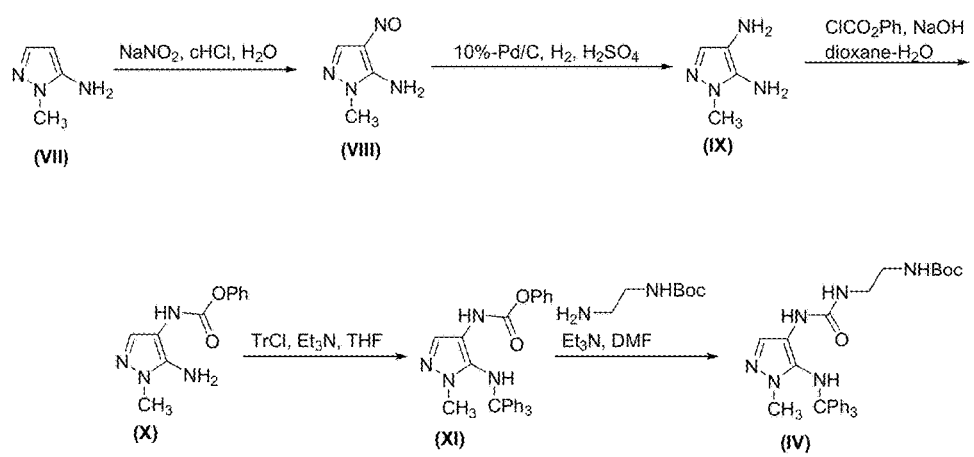
FIG. 2 shows a synthetic scheme to prepare intermediate compound (IV).
Figure 3:
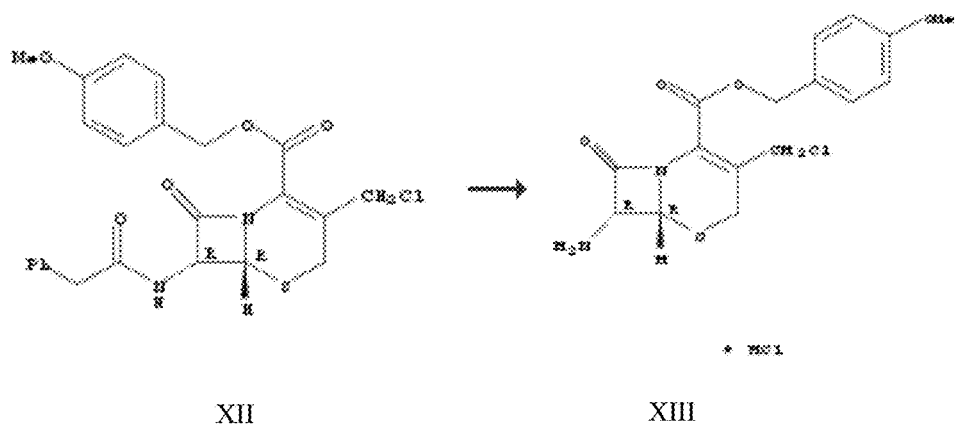
FIG. 3 shows a synthetic scheme to prepare compound (II).

Compound (II) is also known as "ACLE.HCl" and "((6R,7R)-3-(chloromethyl)-2-(((4-methoxybenzyl) oxy)carbonyl)-8-oxo-5-thia-1-azabicyclo[4.2.0]oct-2-en-7-aminium chloride)" and has the structure shown below.

Provided herein is a method of making compound (II):

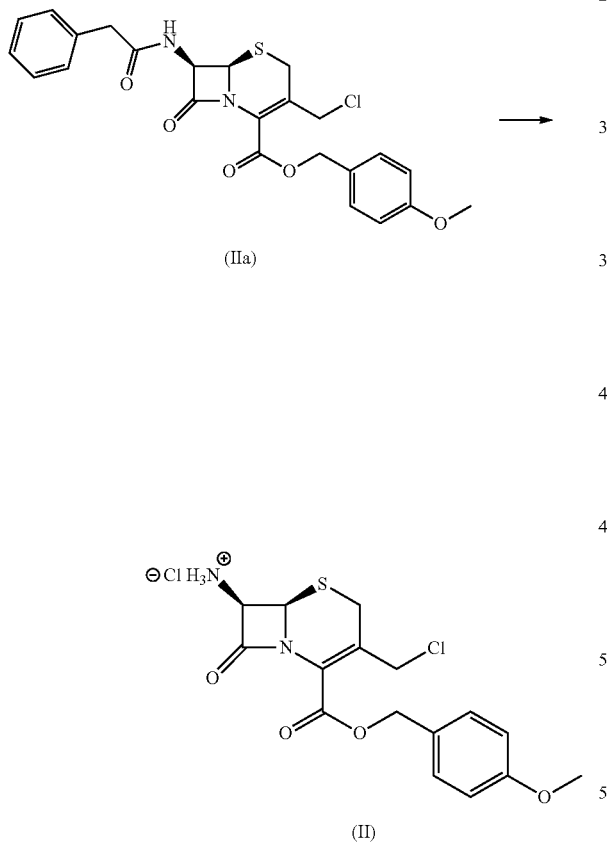

In one aspect, the method comprises the steps of: (a) forming a reaction mixture comprising phosphorous pentachloride (PCl$_5$) and pyridine; (b) adding compound (IIa) to the reaction mixture; (c) adding isobutyl alcohol; (d) adding a solvent comprising water; (e) adding ethyl acetate; and (f) obtaining compound (II). The method can be performed in one or more steps. Unless otherwise indicated, one or more steps may be combined in alternative embodiments of the methods disclosed herein.

In one embodiment, step (a) comprises: (1) combining PCl$_5$ and dichloromethane; and (2) adding pyridine. Step (1) can comprise the steps of: (i) combining 2.0 equivalents PCl$_5$ and 6.0 volumes dichloromethane while maintaining the temperature below 30° C.; and (ii) adjusting the temperature to 10 to 30° C. and agitating. Step (2) can comprise (i) adjusting the temperature to −10 to −5° C.; (ii) adding 2.0 equivalents of pyridine while maintaining the temperature at −10 to 5° C.; and (iii) adjusting the temperature to −5 to 0° C. and agitating.

In one embodiment, step (b) comprises: (1) adding 1.0 equivalent compound (IIa) to the reaction mixture of step (a) while maintaining the temperature of the mixture at −10 to 0° C.; and (2) stirring the mixture at −10 to 0° C. At the completion of step (b), the mixture of step (2) can comprise ≤5.0% compound (IIa) relative to compound (II)+compound (IIa).

In one embodiment, step (c) comprises: (1) adjusting the temperature of the mixture to −20 to −10° C.; (2) adding 2.0 volumes of isobutyl alcohol drop-wise while maintaining the temperature of the mixture at −20 to 5° C.; and (3) agitating the mixture at −10 to 0° C.

In one embodiment, step (d) comprises: (1) adding a solvent comprising water to the mixture of step (c) while maintaining the temperature of the mixture at −10 to 5° C.; (2) agitating the mixture at −5 to 5° C.; and (3) separating a lower organic phase from the mixture and collecting the lower organic phase. In one embodiment of step (d), the solvent comprising water is a mixture of ethanol and water. In another embodiment, step (d) further comprises: (4) adding dichloromethane to the mixture at −10 to 0° C.; (5) agitating the mixture at −10 to 0° C.; and (6) separating a lower organic phase from the mixture and collecting the lower organic phase.

In one embodiment, step (e) comprises: (1) concentrating the organic phase to 4 to 5 volumes; (2) adjusting the temperature to −10 to −5° C.; (3) adding 2.1 volumes of ethyl acetate drop-wise while maintaining the temperature of the mixture at −10 to −5° C.; and (4) agitating the mixture at −10 to 5° C. In another embodiment, step (e) further comprises: (5) observing the formation of a precipitate; (6) concentrating the organic phase to 4 to 5 volumes; (7) adjusting the temperature of the mixture to −10 to −5° C.; (8) adding 2.1 volumes of ethyl acetate while maintaining the temperature of the mixture at −10 to −8° C.; and (9) agitating the mixture at −10 to −5° C.

In one embodiment, step (f) comprises: (1) centrifuging the mixture to produce a cake; and (2) collecting the cake. In another embodiment, step (f) further comprises: (3) adding 2.2 volumes of ethyl acetate; (4) adjusting the temperature to −10 to −5° C.; (5) agitating at −10 to −5° C.; (6) centrifuging to produce a cake; (7) collecting the cake; and (8) drying the cake at 5 to 20° C.

Figure 4:
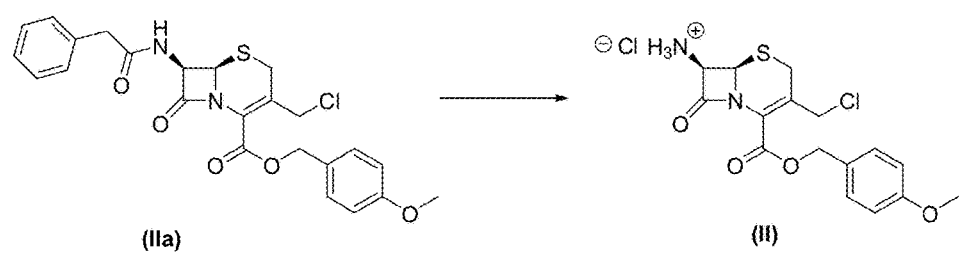
FIG. 4 shows a synthetic scheme to prepare compound (II) from compound (IIa) using a preferred method.

Referring to FIG. 4 and the example below, a preferred method comprises the steps:

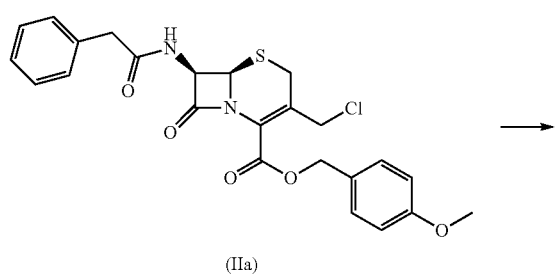

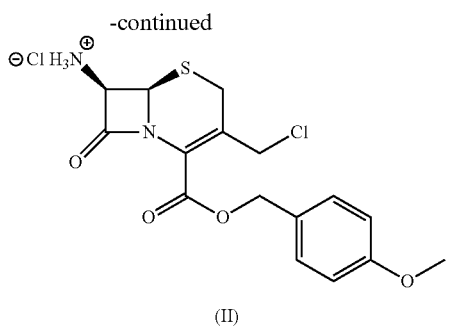

(II)

(1) Preparation of Compound (II)

DCM (2135.4 kg, 6.0 vol.) and PCl$_5$ (230.1 kg, 2.0 eq) were charged to reactor 1, while maintaining the batch temperature below 30° C. The temperature of the batch in reactor 1 was adjusted to 10 to 30° C. and the batch was agitated at 10 to 30° C. for 0.5 to 1.0 hour. The batch temperature was adjusted to −10 to −5° C. Then pyridine (89.4 kg, 2.0 eq) was charged to the batch in reactor 1 drop-wise at −10 to 5° C. The batch temperature was adjusted to −5 to 0° C. and the batch was agitated for 30-40 minutes.

Compound (IIa) (269.8 kg, 1.0 eq) was charged to reactor 1 in portions at −10 to 0° C. The batch was stirred at −10 to 0° C. for 1 to 2 hrs, or until ≤5.0% compound (IIa) was detected by HPLC. Charging compound (IIa) at −10 to 0° C. is critical to prevent epimerization of the C—N(H) bond. See Studies on the Epimerization of compound (II), below.

The batch temperature was adjusted to −20 to −10° C. The adjustment of temperature to −20 to −10° is critical in order to prevent reformation of compound (IIa) in the following step.

The batch was then charged with isobutyl alcohol (446.0 kg, 2.0 vol) drop-wise, while maintaining the batch temperature at −20 to 5° C. The use of isobutyl alcohol prevents the formation of impurities such as ethyl chloride. The batch was agitated at −10 to 0° C. for 0.5 to 2.0 hours. HPLC: (IIa)/[(II)+(IIa)]≤5.0% (Method AM-C11030404-A-01).

(2) Work-Up of Compound (II)

Water (612 kg, 2.3 vol) and EtOH (206.4 kg, 1.0 vol) was charged into reactor 3 and was agitated for at least 5 min. The temperature of reactor 3 was adjusted to −5 to 5° C. The batch in reactor 1 was then transferred to reactor 2. A portion of the solution of water and ethanol (H$_2$O/EtOH: 3:1) (551.4 kg, 2.0 vol) prepared was charged into reactor 2, while maintaining the batch at −10 to 5° C. The contents of reactor 2 were stirred at −5 to 5° C. for at least 10 min. The agitation was stopped and the phases were allowed to separate for at least 10 minutes. The lower organic phase is transferred to reactor 1. DCM (148.0 kg, 0.41 vol) was charged to reactor 2 and the batch was agitated for 10 to 20 min at −10 to 0° C. The agitation was stopped and the phases were allowed to separate at −10 to 0° C. for at least 10 minutes and then the lower organic layer was transferred to reactor 1. The rest of the solution of water and ethanol (H$_2$O/EtOH: 3:1) (270 kg, 1.0 vol) was charged into the batch in reactor 1 at −10 to 0° C. The contents of reactor 1 was agitated at −10 to 0° C. for 20 to 30 minutes. The agitation was then stopped and the phases were allowed to separate for at least 10 minutes. HPLC: (IIa)/[(II)+(IIa)]≤5.0% (Method AM-C11030404-A-01). The contents of reactor 2 were agitated at −10 to 0° C. for 5 to 10 min. The agitation was then stopped and the phases were allowed to separate at −10 to 0° C. for at least 10 minutes. The lower organic phase was transferred to reactor 1. The solvents, reagents, stoichiometry, temperatures and reaction times of step (2) were selected to increase yield and reaction efficiency.

(3) Isolation of Compound (II)

The organic phase in reactor 1 was concentrated at ≤25° C. jacket temperature to 1076 to 1345 L (4 to 5 vol) under reduced pressure. Then the batch temperature was adjusted to −10 to −5° C. Ethyl Acetate (513.0 kg, 2.1 vol) was charged drop-wise to the batch at −10 to −5° C. for 2 to 4 hours. Then the batch was agitated at −10 to −5° C. for 5 to 6 hours. A precipitate forms. The agitation was continued until ≤2.0% of compound (II) was detected in the supernatant by HPLC. If compound 2 is >2% then the batch temperature was adjusted to −5 to 5° C. and concentrated at ≤25° C. jacket temperature to 1076 to 1345 L (4 to 5 vol) under reduced pressure. Then the temperature was adjusted to −10 to −5° C. Ethyl Acetate (513.0 kg, 2.1 vol) was charged drop-wise to the batch at −10 to −8° C. over the course of 2 to 4 hours. Then the batch was agitated at −10 to −5° C. for 5 to 10 hours. HPLC: Compound (II) in supernatant ≤2.0% (Method AM-C11030404-A-01).

The batch was centrifuged and the wet cake was collected. Ethyl Acetate (540.0 kg, 2.2 vol) was charged into reactor 1. The wet cake was transferred into reactor 1. The temperature in reactor 1 was adjusted to −10 to −5° C. and the batch was agitated at −10 to −5° C. for 2 to 5 hours. The batch was centrifuged and the wet cake was collected. HPLC: Pyridine ≤0.1%; (IIa) ≤0.1%; total purity ≥97% (Method AM-C11030404-A-01).

The solid was dried under reduced pressure at 5 to 20° C. for 40 to 70 hours. The batch was deemed dry when: water ≤0.4%; EtOAc ≤5000 ppm; Ethanol ≤5000 ppm; DCM ≤6000 ppm; i-BuOH ≤5000 ppm. Yield 198.7 kg (87% molar yield) of compound (II) with 99% purity using HPLC method AM-C11030404-A-01.

TABLE 1

Materials for the preparation of Compound (II)

| Material | MW. (g/mol) | Weight (kg) | Moles | Equivalents | Mass (w/w) | Density |
|---|---|---|---|---|---|---|
| (IIa) | 486.97 | 269.8 | 0.55 | 1.0 | 1.00 | |
| PCl$_5$ | 208.24 | 230.1 | 1.11 | 2.0 | 0.85 | |
| Pyridine | 79.10 | 89.4 | 1.13 | 2.0 | 0.33 | |
| DCM | | 2135.4 | | | 7.92 | 1.33 |
| i-Butyl alcohol | | 446.0 | | | 1.65 | 0.81 |
| H$_2$O | | 612 | | | 2.27 | 1.00 |
| EtOH | | 206.4 | | | 0.77 | 0.80 |
| DCM | | 148.0 | | | 0.55 | 1.33 |
| EtOAc | | 513.0 | | | 2.11 | 0.90 |
| EtOAc | | 540.0 | | | 2.00 | 0.90 |
| (II) (theoretical) | 405.30 | 224.5 | | | | |
| (II) (isolated) | 405.30 | 198.7 | | | | |

Studies on the Epimerization of Compound (II)

The purpose of this study was to test the robustness of the manufacturing process for making compound (II) (ACLE-HCl) from compound (IIa) (GCLE) and to better understand the origin of impurity (peak 8) in the Ceftolozane drug substance. This impurity was observed at 0.03% in the Ceftolozane drug substance. The impurity was isolated by Prep-HPLC and its structure was determined to be the 7-epimer of Ceftolozane by HRMS and NMR analysis.

Figure 6:
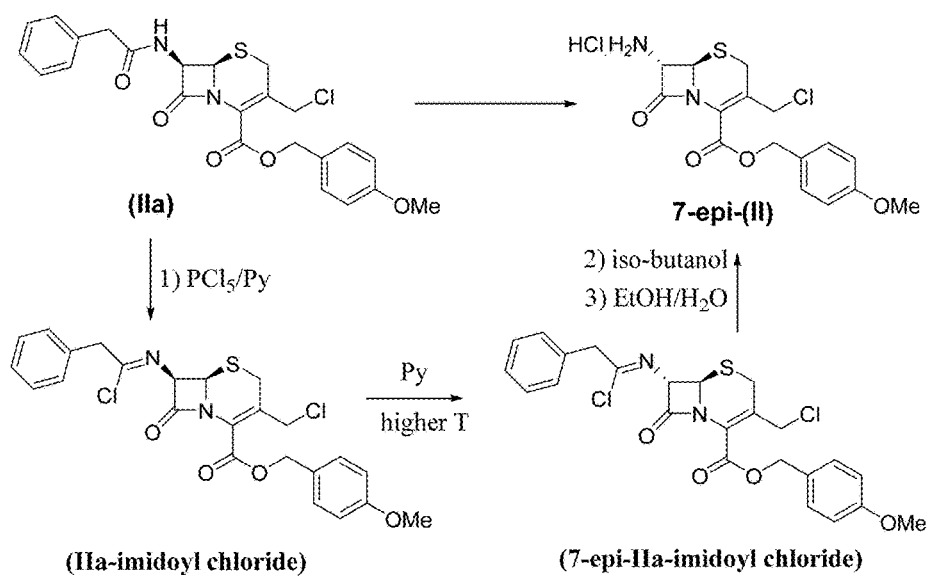
FIG. 6 shows the mechanism for the cleavage of an amide side chain of β-lactam antibiotics with PCl$_5$.

The starting material ACLE-HCl was prepared from GCLE by treatment with phosphorus pentachloride and pyridine in dichloromethane, followed by alcoholysis with isobutanol. As shown in FIG. 6, the mechanism for the cleavage of the amide side chain involves the formation of intermediate imidoyl chloride. In the present case, the reaction temperature was intentionally raised to explore the possibility of epimerization of the imidoyl chloride. In order to identify the 7-epimer of ACLE-HCl peak in the HPLC and provide standard 7-epi-ACLE-HCl for quality control, a synthetic route to provide this material was also developed.

I. Preparation of ACLE-HCl at Elevated Temperature

TABLE A

List of Materials

| Material | MW | Weight (g) | mMoles | Ratio eq. | (w/w) | Density |
|---|---|---|---|---|---|---|
| GCLE | 486.97 | 10.0 | 20.54 | 1 | 1X | |
| PCl$_5$ | 208.24 | 8.55 | 41.07 | 2.0 | 0.86X | |
| pyridine | 79.1 | 3.30 | 45.18 | 2.0 | 0.33X | |
| DCM | | 80.0 | | | 8X | 1.33 |
| iso-butyl alcohol | | 16.2 | | | 1.62X | 0.81 |
| H$_2$O | | 10.0 | | | 1X | 1.0 |
| EtOH | | 36.0 | | | 3.06X | 0.8 |
| EtOAc | | 108.0 | | | 10.8X | 0.9 |
| ACLE-HCl (theoretical) | 405.3 | 8.32 | | | | |
| ACLE-HCl (isolated) | 405.3 | 5.83 | | | | |
| Isolated yield | | 70% | | | | |

II. Process Steps
1. Charged 80.0 g (6 V) DCM into Reactor 1 (R1).
2. Charged 8.55 g (2 eq) PCl$_5$ into R1 at room temperature (RT).
3. Stirred R1 at 20 to 25° C. for 0.5 h.
4. Cooled R1 to −10 to 0° C.
5. Added 3.3 g (2.0 eq) pyridine into R1 drop-wise at −10 to 5° C.
6. Stirred R1 for 0.5 h at −5 to 5° C.
7. Charged 10.0 g GCLE into R1 at −10 to 0° C.
8. Warmed to RT.
9. Stirred at 35 to 40° C. for 1 h using warm water.
10. Cooled R1 to −20 to −10° C.
11. Added 16.2 g isobutyl alcohol into R1 drop-wise at −20 to −10° C.
12. Stirred R1 at −10 to 0° C. for 2 h.
13. Charged 20.0 g (2.0×) EtOH:H$_2$O (1:3) into R1 at −10 to 5° C.
14. Stirred R1 at −10 to 5° C. for 1 h.
15. Allowed phase separation at −10 to 0° C.
16. Aqueous layer was extracted with 5 g DCM, stirred for 30 min at −10 to 0° C.
17. Allowed phase separation at −10 to 0° C.
18. Combined organic layer in R2 charged with 10 g EtOH:H$_2$O (1:3) at −10 to 0° C.
19. Stirred R2 for 30 min at −10 to 0° C.
20. Allowed phase separation at −10 to 0° C.
21. To the organic layer was charged 10 g water.
22. Stirred for 30 min at −10 to 0° C.
23. Allowed phase separation at −10 to 0° C.
24. Organic layer was filtered and washed with DCM (2 mL).
25. Organic layer was concentrated to ~28 g using evaporator at 20° C. (≤25° C.).
26. Charged EtOAc (18 g) at −10 to −5° C.
27. The slurry was stirred for 5 h at −10 to −5° C.
28. Organic layer was concentrated to ~28 g using evaporator at 20° C. (≤25° C.).
29. The slurry was stirred for 5 h at −10 to −5° C.
30. The slurry was cooled to −10 to 0° C., and stirred for 1 h.
31. Filtration to collect the solid, washed with EtOAc (3 mL).
32. Dried solid under vacuum with N$_2$ purge overnight (5.83 g, yield 70%, purity 94~95%).

III. Preparation of (Epi-II) (7-Epi-ACLE-HCl)

Figure 7:
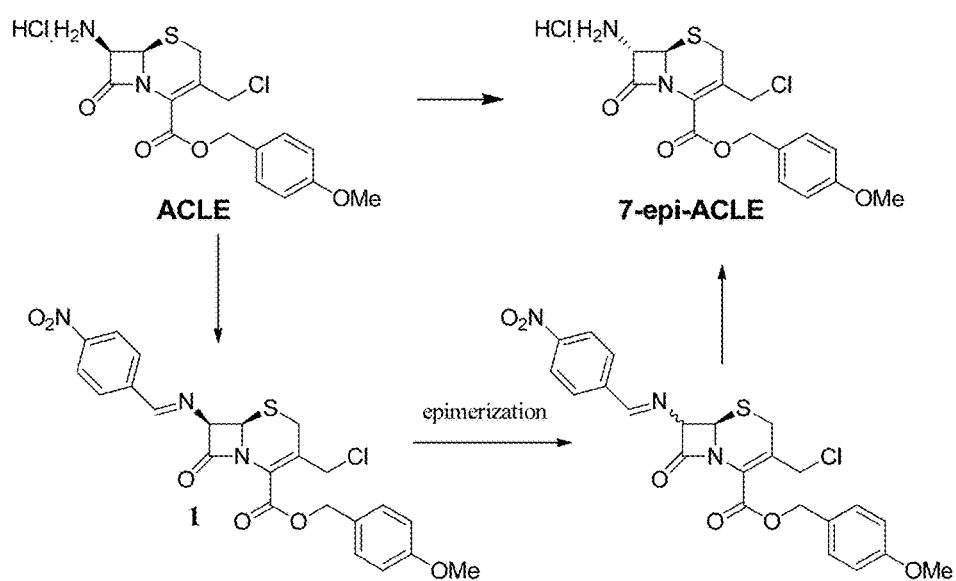
FIG. 7 shows the preparation of compound (epi-II) (7-epi-ACLE-HCl).

With reference to FIG. 7, compound (epi-II) was prepared as follows:

Preparation of p-nitrobenzaldehyde imine (1): To a stirred suspension of ACLE-HCl (22.3 g, 55.0 mmol) in ethyl acetate (200 mL) and water (75 mL) was added 1 N aq. NaOH (100 mL) at 0° C. After addition, the mixture was stirred for 30 min. to give a clear two-phase solution. The EtOAc layer was separated, washed with water (2×75 mL) and dried with Na$_2$SO$_4$ (50 g). To above suspension was added p-nitrobenzaldehyde (9.8 g, 65.0 mmol). The mixture was stirred at R. T. for 2 h, then diluted with DCM (400 mL). The Na$_2$SO$_4$ was removed by filtration and washed with DCM. The filtrate was concentrated to give a paste, which was filtered and washed with 10% EtOAc in hexanes to give a yellowish solid. The solid was dried under in-house vacuum with N$_2$ purge to provide the imine (23.6 g, 85.5%). 1H NMR (CDCl$_3$) δ 8.73 (1H, d, J=1.8 Hz), 8.30 (2H, d, J=8.7 Hz), 7.97 (2H, d, J=8.7 Hz), 7.39 (2H, d, J=8.7 Hz), 6.93 (2H, d, J=8.7 Hz), 5.50 (1H, dd, J=1.8, 5.1 Hz), 5.27 (2H, s), 5.22 (1H, d, J=5.1 Hz), 4.59 (1H, d, J=12.0 Hz), 4.42 (1H, d, J=12.0 Hz), 3.84 (3H, s), 3.71 (1H, d, J=18.3 Hz), 3.48 (1H, d, J=18.3 Hz).

Epimerization: To a solution of imine 1 (10.34 g, 20.6 mmol) in THF (200 mL) was added NEt$_3$ (100 mg, 1 mmol) at 0° C. Within 2 min., the reaction was quenched by adding acetic acid (200 mg), diluted with EtOAc (50 mL) and water (50 mL). The EtOAc layer was separated, washed with water and brine, dried over Na$_2$SO$_4$. After filtration, the filtrate was concentrated to give a mixture of the imines (13 g, 7α:7β~1:2.5). The two isomeric imines can be separated by flash chromatography, even though they will decompose during the chromotagraphy. For 7α imine: 1H NMR (CDCl$_3$) δ 8.54 (1H, d, J=1.2 Hz), 8.29 (2H, d, J=8.7 Hz), 7.93 (2H, d, J=8.7 Hz), 7.39 (2H, d, J=8.7 Hz), 6.90 (2H, d, J=8.7 Hz), 5.34 (1H, d, J=12.0 Hz), 5.24 (1H, d, J=12.0 Hz), 4.96 (1H, d, J=2.1 Hz), 4.88 (1H, dd, J=1.2, 2.1 Hz), 4.48 (1H, d, J=12.0 Hz), 4.39 (1H, d, J=12.0 Hz), 3.80 (3H, s), 3.73 (1H, d, J=18.0 Hz), 3.50 (1H, d, J=18.0 Hz).

Preparation of 7-epi-ACLE-HCl: To a mixture of 2, 4-dinitrophenylhydrazine (3.96 g, 20 mmol), p-toluenesulfonic acid monohydrate (3.80 g, 20 mmol) in ethanol (800 mL) was added the above prepared imine mixture (13 g) in CHCl$_3$ (60 mL) at RT. After addition, the mixture was stirred at RT for 4 hrs until the completion of the reaction indicated by TLC. The orange precipitate was removed by filtration, washed with ethanol (20 mL). The filtrate was put into the fridge overnight. The precipitate (2.1 g) was collected by filtration, washed with ethanol (20 mL). 1H NMR showed that the precipitate was ACLE-p-TSA salt. The filtrate was then concentrated to about 400 mL and put into the fridge overnight. The precipitate (0.6 g) was collected by filtration, washed with ethanol (10 mL). The mother liquor was concentrated to give a residue (~7.0 g), which was mixed with EtOAc (200 mL) and water (30 mL). To above mixture, 1 N aq. NaOH (30 mL) was added at 0° C. and the mixture was stirred for 30 min at 0° C. to become a clear two-phase solution. The EtOAc layer was separated, washed with water, brine and dried over Na$_2$SO$_4$. After filtration, filtrate was concentrated to about 100 mL, then 2 N HCl in ether (20 mL) was added at 0° C. and the mixture was stirred at 0° C. for half an hour. The solid was collected by filtration, washed with EtOAc and dried in vacuum to give a brown solid (2.7 g, 7-epi-ACLE-HCl:ACLE-HCl~2.5:1). The above solid (100 mg) was crystallized with methanol/acetonitrile to give (~20 mg) pretty pure 7-epi-ACLE-HCl. 1H NMR (DMSO-d6) δ 8.98 (3H, b), 7.39 (2H, d, J=8.0 Hz), 6.95 (2H, d, J=8.0 Hz), 5.30 (1H, d, J=11.6 Hz), 5.21 (1H, d, J=11.6 Hz), 5.04 (1H, s), 4.77 (1H, s), 4.48 (1H, d, J=11.6 Hz), 4.42 (1H, d, J=11.6 Hz), 3.85 (1H, d, J=18.4 Hz), 3.77 (3H, s), 3.56 (1H, d, J=18.4 Hz) (FIG. 7).

For ACLE-p-TSA salt: 1H NMR (DMSO-d6) δ 8.84 (3H, b), 7.48 (2H, d, J=7.6 Hz), 7.37 (2H, d, J=7.6 Hz), 7.11 (2H, d, J=7.6 Hz), 6.94 (2H, d, J=7.6 Hz), 5.18~5.28 (4H, m), 4.59 (1H, d, J=11.6 Hz), 4.49 (1H, d, J=11.6 Hz), 3.82 (1H, d, J=17.6 Hz), 3.76 (3H, s), 3.69 (1H, d, J=17.6 Hz), 2.29 (3H, s).

IV. HPLC conditions

HPLC column: YMC Pack-ODS-AQ, 3 μm, 150 mm×4.6 mm
Injection Volume: 10μ+l
Column Temp: 20±2° C.
Autosampler Temp: 4+° C.
Wavelength: 254 nm
Mobile Phase A: Buffer Ammonium Acetate Solution: Dissolve 4.0 g of NH4OAc in 0.9 L of water in a 1 L volumetric flask, using a calibrated pH meter, adjust the pH to 3.5±0.05 with acetic acid and dilute to volume with water. Mix well by magnetic stirrer or by inversion. Mix 450 mL of buffer ammonium acetate solution and 550 mL CAN. Mix well to become the mobile phase A solution.
Mobile Phase B: Acetonitrile
Flow rate: 1.0 mL/min
Run Time: 30 min
Mode: Gradient (see Table B)

TABLE B

| Time (min) | % A | % B |
| --- | --- | --- |
| 0.00 | 100 | 0 |
| 12.00 | 100 | 0 |
| 22.00 | 40 | 60 |
| 23.00 | 100 | 0 |
| 30.00 | 100 | 0 |

V. Results and Discussion

Figure 8:
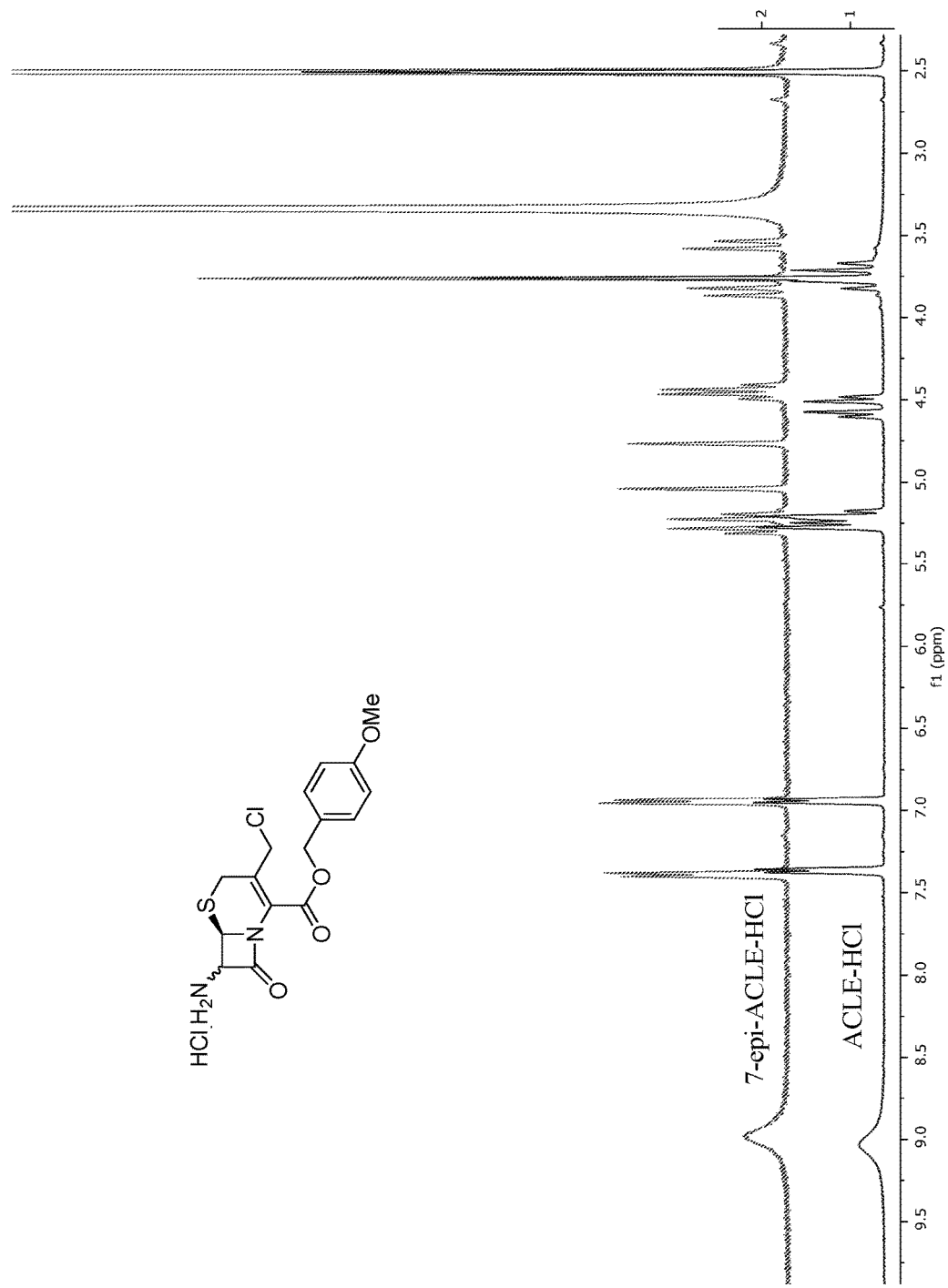
FIG. 8 shows a comparison of compound (epi-II) and compound (II) $^1$HNMR spectra.
Figure 9:
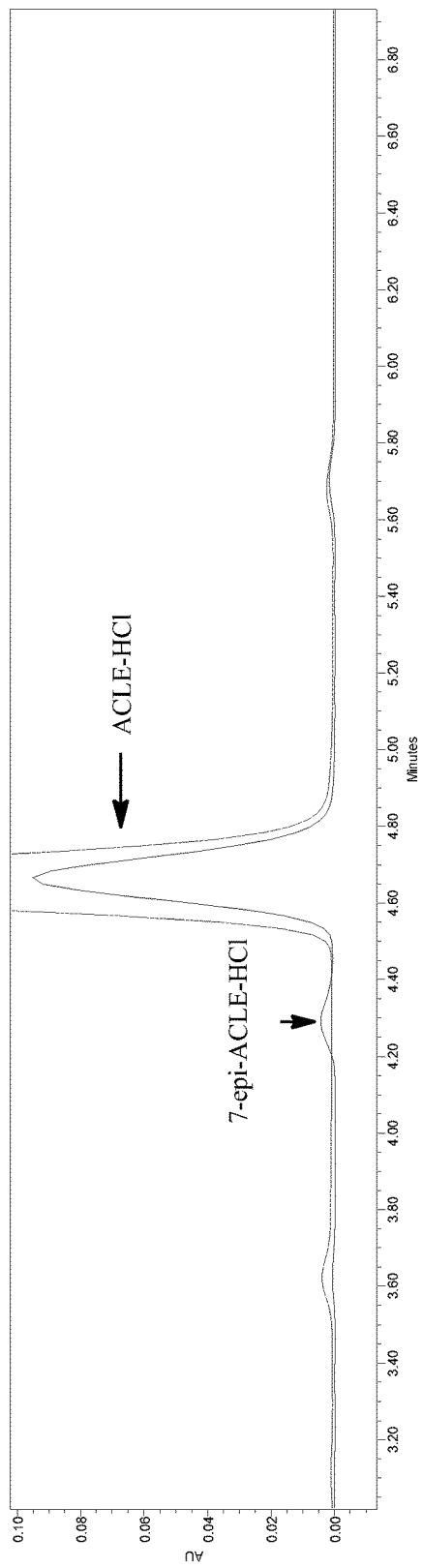
FIG. 9 shows HPLC traces of compound (II) made at 35~40° C. and a compound (II) standard.
Figure 10:
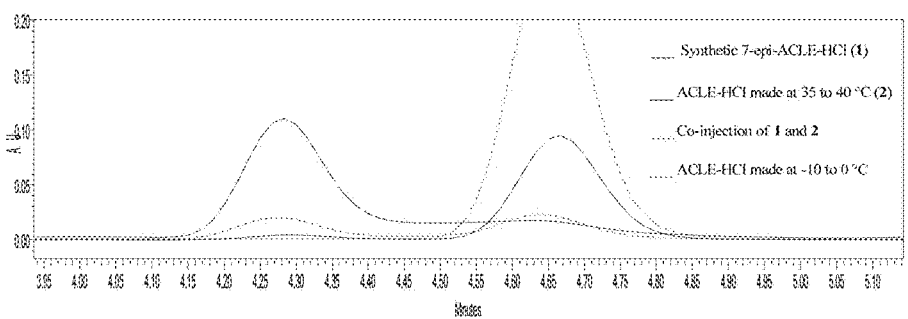
FIG. 10 shows a comparison of the chromatograms of four reactions in the epimerization study.
Figure 11:
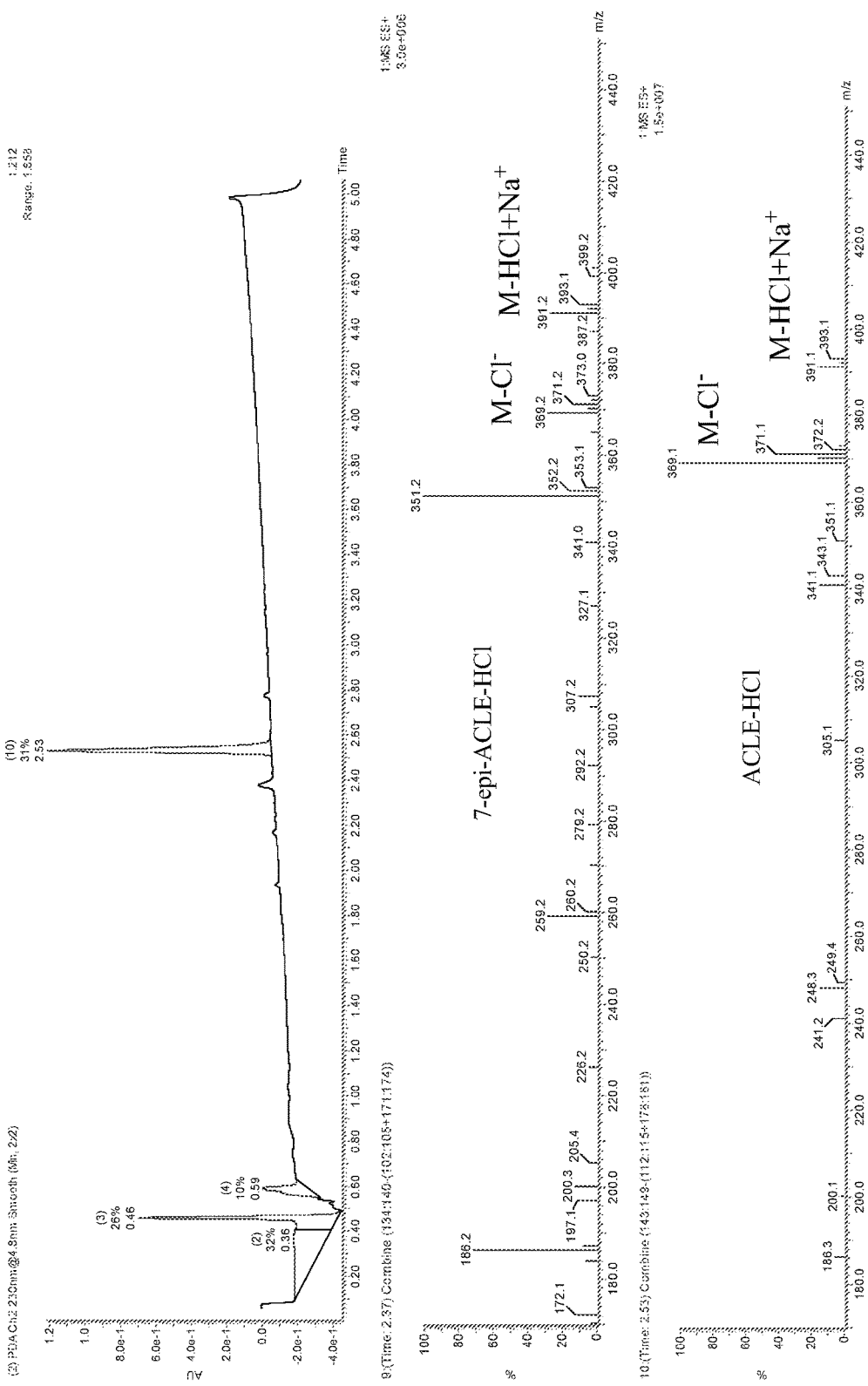
FIG. 11 shows LCMS analysis of compound (II) made at 35 to 40° C.
Figure 12:
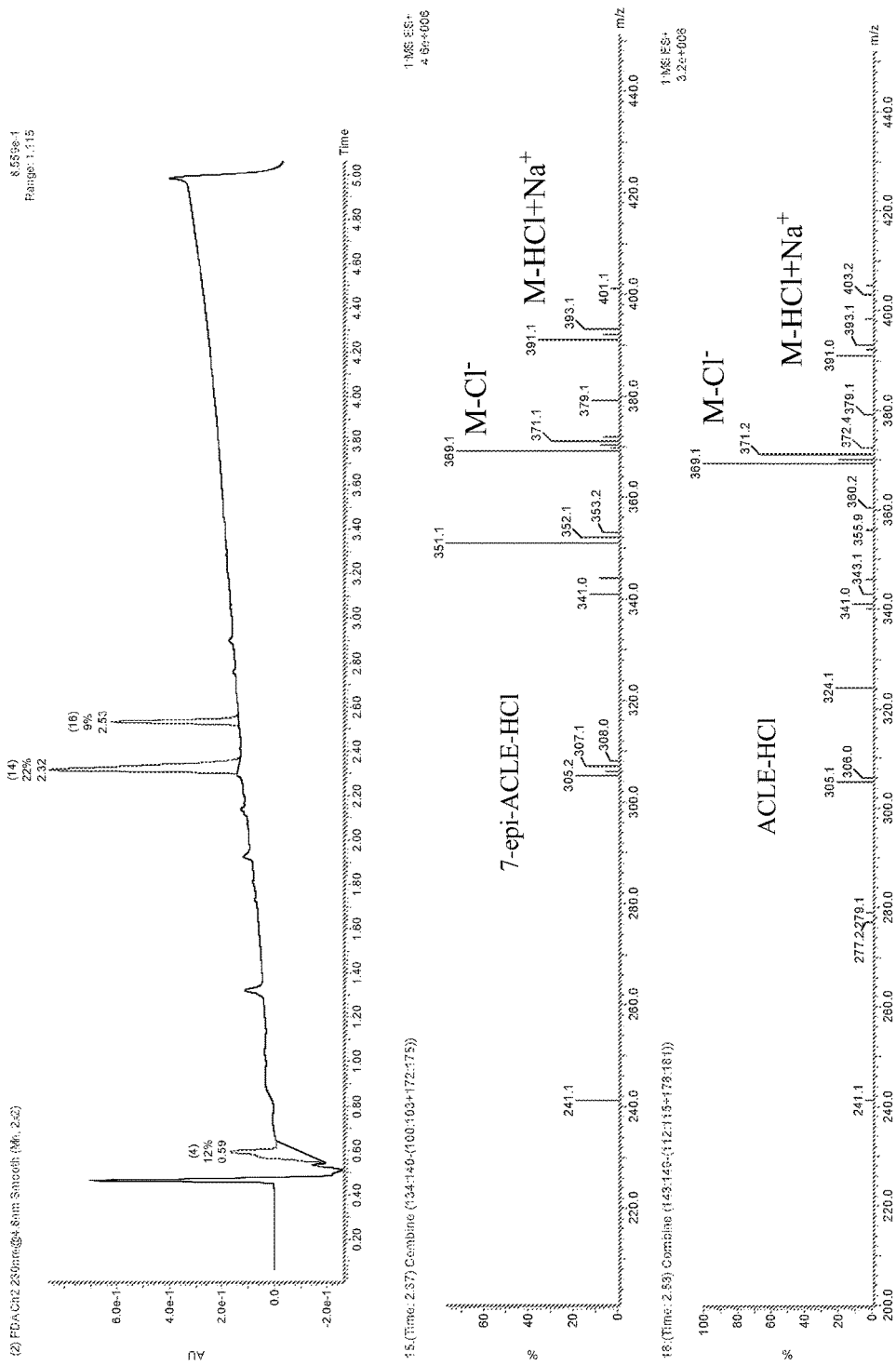
FIG. 12 shows LCMS analysis of synthetic mixture of compound (epi-II) and compound (II).

The ACLE-HCl prepared at elevated temperature, as described above, was analyzed by HPLC and LCMS. As seen in the HPLC trace, the product showed a similar profile as the in-house standard except for a new peak at 4.29 (FIG. 8). This peak, coeluting with synthetic 7-epi-ACLE-HCl (FIG. 9) and showing similar MS pattern as ACLE-HCl (FIG. 10), was identified as 7-epi-ACLE-HCl. The synthetic mixture of 7-epi-ACLE-HCl and ACLE-HCl also showed very similar LCMS profiles as this sample (FIG. 11) which further confirmed the identity of the new peak. The ratio between 7-epi-ACLE-HCl and ACLE-HCl was about 1:34.4.

Control of the reaction temperature after the charge of GCLE is important in the manufacturing of ACLE-HCl from GCLE. When the reaction temperature was raised from −10~0° C. to 35~40° C., a small amount of 7-epi-ACLE-HCl (about 2~3%) was observed in the product. 7-epi-ACLE-HCl was not detected in the in-house standard of ACLE-HCl (Table C).

TABLE C

Effect of Temperature on the Ration of 7-epi-ACLE-HCl to ACLE-HCl

| Temperature | 7-epi-ACLE-HCl (% AUC) | ACLE-HCl (% AUC) |
| --- | --- | --- |
| −10 to 0° C. | 0 | 100 |
| 35 to 40° C. | 2.8 | 97.2 |

Characterization of Compound (II)

(1) HPLC Method AM-C11030404-A-01: Assay by external standard analysis with a gradient, reversed-phase (RP) HPLC method using a YMC-Pack-ODS-AQ (150×4.6 mm i.d., 3 m) or equivalent column. Mobile phase A is a mixture of ammonium acetate in water (4 g/L) adjusted to pH 3.5 and acetonitrile (v/v 45:55), and mobile phase B is acetonitrile. UV detection is at 254 nm.

(2) Optical rotation: Analysis is performed on a 10 mg/mL solution in dimethylformamide at 589 nm at 20±0.5° C. Acceptance criterion for optical rotation of ACLE.HCl is −58° to −47° which is supported by the batch analysis mean of 9 batches plus and minus three standard deviations. Optical rotation values from the 9 batches ranged from −54.2° to −50.7°.

(3) Water content of ACLE.HCl was measured by Karl Fischer titration.

(4) FTIR: The IR absorption spectrum (KBr dispersion) was recorded in the range of 4000 to 650 cm 1.

(5) Impurities: Dichloro-PMB ester (IIb) and 7-Epi-ACLE.HCl (epi-II).

Figure 5:
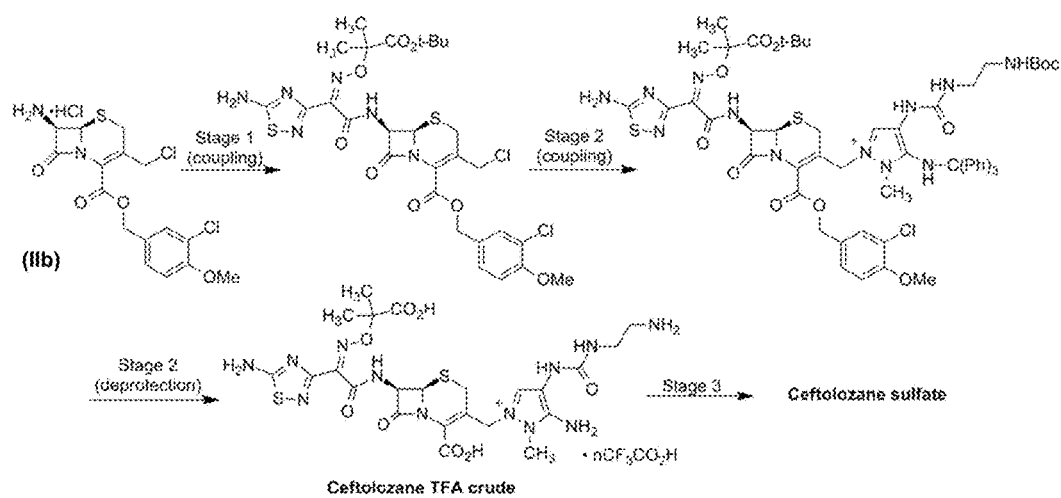
FIG. 5 shows the chemical structure and fate of Dichloro-PMB ester (compound (IIb)).

The most abundant impurity in ACLE.HCl produced by the above procedure is the compound "Dichloro-PMB ester" (see FIG. 5), also referred to as compound IIb. The structure of (IIb) ester comprises an additional chlorine atom on the aromatic ring of the para-methoxybenzyl protecting group. Compound (IIb) is present in ACLE.HCl at levels ranging from 0.76% to 0.97%. This impurity has essentially the same reactivity as ACLE.HCl and is converted to ceftolozane during the subsequent processing steps, as shown in FIG. 5.

7-Epi-ACLE.HCl (epi-II) is described above.

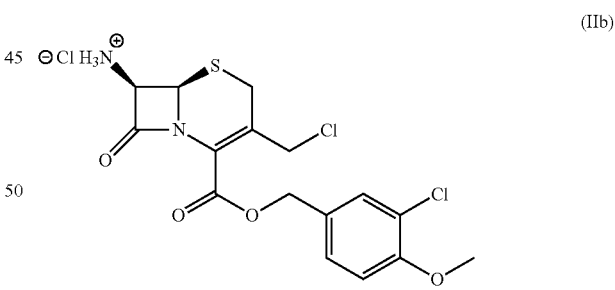

(IIb)

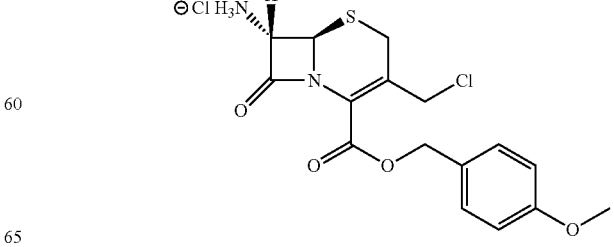

(epi-II)

(6) X-Ray Powder Diffraction.

Figure 13:
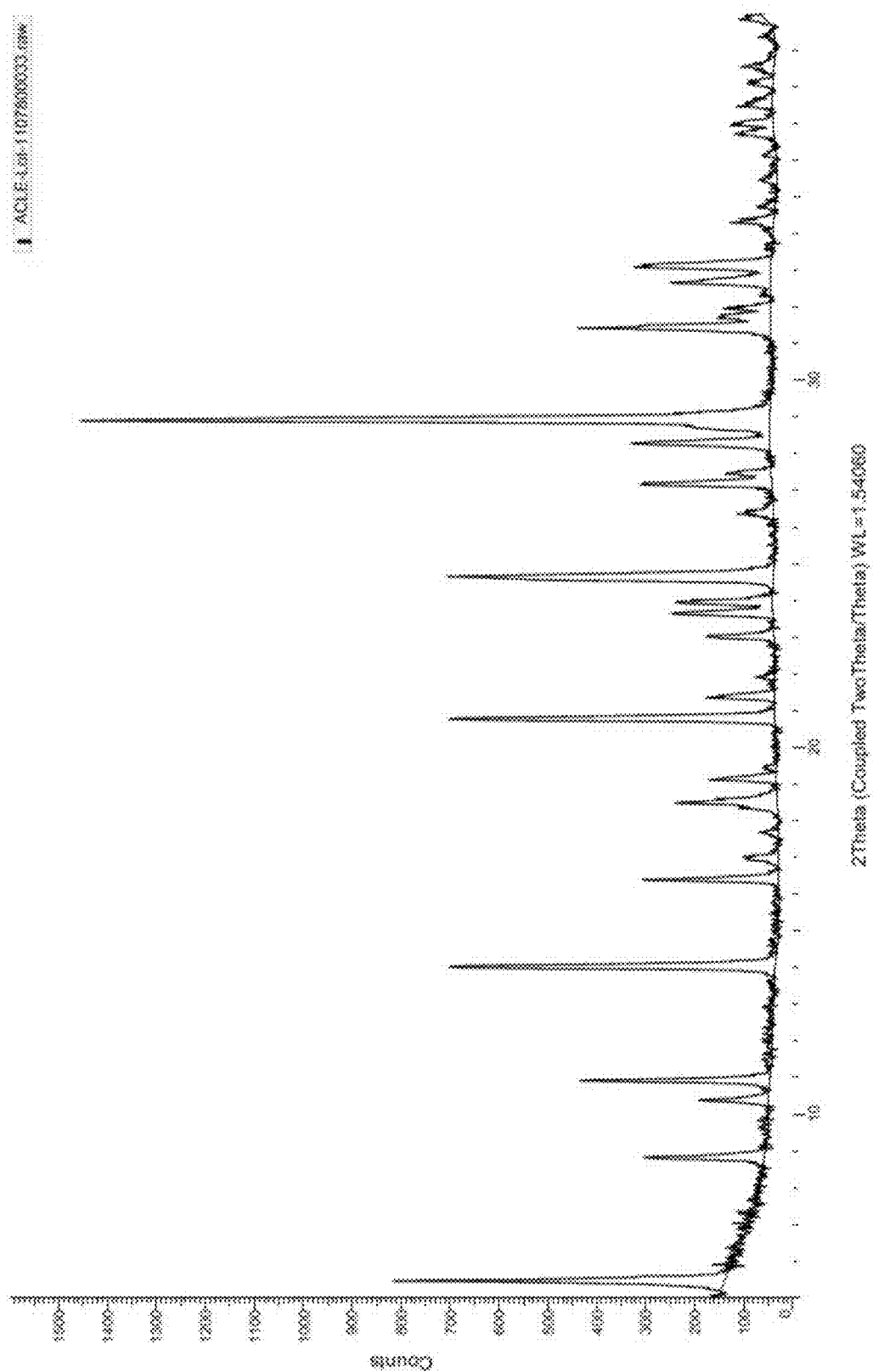
FIG. 13 shows and XRPD pattern for a crystal form of compound (II).

Provided herein is a crystal form of compound (II). In one embodiment, the crystal form of compound (II) exhibits an X-ray powder diffraction spectrum having characteristic peaks at substantially the same angles as the pattern of FIG. 13.

Synthetic Compositions

Compound (II) is a useful intermediates in the production of antibiotics, particularly ceftolozane, and salts thereof. Compositions comprising compound (II) are provided herein. Also provided are compositions produced or occurring during the methods of making compound (II).

The following composition may be produced during method 2: a composition comprising compounds (IIa) and (II); a composition comprising compounds (II) and (IIb); and a composition comprising compounds (II) and (epi-II).

TABLE 2

Analytical Test Results

| Analytical Test | Analytical Method | Target Results | Typical Result |
|---|---|---|---|
| Consumption of (IIa) | HPLC | ≤5.0% | 4.9% |
| Consumption of (IIa) | HPLC | ≤5.0% | 1.8% |
| Consumption of (IIa) | HPLC | Report | 2.0% |
| Residue of (II) in supernatant | HPLC | ≤2.0% | 0.4% |
| Purity of (II) in wet cake | HPLC | ≥97% | 99% |
| Residue of (IIa) in wet cake | HPLC | ≤0.1% | 0.07% |
| Pyridine in wet cake | HPLC | ≤0.1% | <0.05% |
| KF in (II) during drying | KF | ≤0.4% | 0.1% |
| EtOAc in (II) during drying | GC | ≤5000 ppm | 39959 ppm |
| Ethanol in (II) during drying | GC | ≤5000 ppm | 620 ppm |
| DCM in (II) during drying | GC | ≤6000 ppm | 3780 ppm |
| i-BuOH in (II) during drying | GC | ≤5000 ppm | 567 ppm |

TABLE 3

Batch Analysis Data for ACLE•HCl: Optical Rotation

| Batch # | Optical Rotation (°) |
|---|---|
| 1 | −51.0 |
| 2 | −50.7 |
| 3 | −51.7 |
| 4 | −52.7 |
| 5 | −52.9 |
| 6 | −51.5 |
| 7 | −53.3 |
| 8 | −54.2 |
| 9 | −54.0 |

We claim:

1. A process for making a compound of the formula (II):

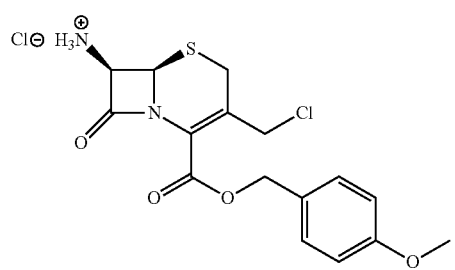

comprising the steps of:
(a) forming a reaction mixture comprising phosphorous pentachloride ($PCl_5$) and pyridine;
(b) adding a compound of the formula (IIa) to the reaction mixture:

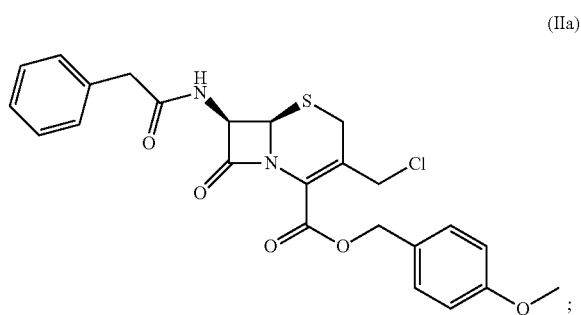 [SMILES: COc1ccc(COC(=O)C2=C(CCl)CS[C@@H]3[C@H](NC(=O)Cc4ccccc4)C(=O)N23)cc1]

(c) adding isobutyl alcohol;
(d) adding a solvent comprising water;
(e) adding ethyl acetate; and
(f) obtaining the compound of the formula (II).

2. The process of claim 1, wherein step (a) comprises:
(1) combining $PCl_5$ and dichloromethane; and
(2) adding pyridine.

3. The process of claim 2, wherein step (1) comprises:
(i) combining 2.0 equivalents $PCl_5$ and 6.0 volumes dichloromethane while maintaining the temperature below 30° C.; and
(ii) adjusting the temperature to 10 to 30° C. and agitating.

4. The process of claim 2, wherein step (2) comprises:
(i) adjusting the temperature to −10 to −5° C.;
(ii) adding 2.0 equivalents of pyridine while maintaining the temperature at −10 to 5° C.; and
(iii) adjusting the temperature to −5 to 0° C. and agitating.

5. The process of claim 1, wherein step (b) comprises:
(1) adding 1.0 equivalent compound (IIa) to the reaction mixture of step (a) while maintaining the temperature of the mixture at −10 to 0° C.; and
(2) stirring the mixture at −10 to 0° C.

6. The process of claim 5, wherein the mixture of step (2) comprises ≤5.0% compound (IIa) relative to compound (II)+compound (IIa).

7. The process of claim 1, wherein step (c) comprises:
(1) adjusting the temperature of the mixture to −20 to −10° C.;
(2) adding 2.0 volumes of isobutyl alcohol dropwise while maintaining the temperature of the mixture at −20 to 5° C.; and
(3) agitating the mixture at −10 to 0° C.

8. The process of claim 1, wherein step (d) comprises:
(1) adding a solvent comprising water to the mixture of step (c) while maintaining the temperature of the mixture at −10 to 5° C.;
(2) agitating the mixture at −5 to 5° C.; and
(3) separating a lower organic phase from the mixture and collecting the lower organic phase.

9. The process of claim 8, wherein the solvent comprising water is a mixture of ethanol and water.

10. The process of claim 8, which further comprises:
(4) adding dichloromethane to the mixture at −10 to 0° C.;
(5) agitating the mixture at −10 to 0° C.; and
(6) separating a lower organic phase from the mixture and collecting the lower organic phase.

11. The process of claim 1, wherein step (e) comprises:
(1) concentrating the organic phase to 4 to 5 volumes;
(2) adjusting the temperature to −10 to −5° C.;
(3) adding 2.1 volumes of ethyl acetate dropwise while maintaining the temperature of the mixture at −10 to −5° C.; and
(4) agitating the mixture at −10 to 5° C.

12. The process of claim 11, wherein step (e) further comprises:
(5) observing the formation of a precipitate;
(6) concentrating the organic phase to 4 to 5 volumes;
(7) adjusting the temperature of the mixture to −10 to −5° C.;
(8) adding 2.1 volumes of ethyl acetate while maintaining the temperature of the mixture at −10 to −8° C.; and
(9) agitating the mixture at −10 to −5° C.

13. The process of claim 1, wherein step (f) comprises:
(1) centrifuging the mixture to produce a cake; and
(2) collecting the cake.

14. The process of claim 13, wherein step (f) further comprises:
(3) adding 2.2 volumes of ethyl acetate;
(4) adjusting the temperature to −10 to −5° C.;
(5) agitating at −10 to −5° C.;
(6) centrifuging to produce a cake;
(7) collecting the cake; and
(8) drying the cake at 5 to 20° C.

\* \* \* \* \*